United States Patent [19]

Alabaster et al.

[11] 4,404,392
[45] Sep. 13, 1983

[54] RESOLUTION OF
α-PIVALOYLOXYETHYL-(S)-3-(3,4-DIHY-
DROXYPHENYL)-2-METHYLALANTINATE
INTO ITS α AND β ISOMERS

[75] Inventors: Ramon J. Alabaster, Puckeridge;
Stanley H. B. Wright,
Sawbridgeworth, both of England

[73] Assignee: Merck & Co., Inc., Rahway, N.J.

[21] Appl. No.: 321,498

[22] Filed: Nov. 16, 1981

[51] Int. Cl.³ ............................................ C07C 101/32
[52] U.S. Cl. ..................................... 560/40; 562/401;
562/446
[58] Field of Search ................... 560/40; 562/401, 446

[56]  References Cited
U.S. PATENT DOCUMENTS 3,983,138  9/1976  Saari ............................. 260/326.43
3,988,341  11/1976  Saari et al. ................... 260/281 GN

OTHER PUBLICATIONS

Saari et al., Journal of Medicinal Chemistry 21 746 (1978).

Primary Examiner—Natalie Trousof
Assistant Examiner—Vera C. Clarke
Attorney, Agent, or Firm—Alice O. Robertson; Ernest V. Linek

[57]  ABSTRACT

Resolution of the α and β isomers of α-pivaloyloxyethyl-(S)-3-(3,6-dihydroxyphenyl)-2-methylalaninate is accomplished by; (a) forming the (+) hydrogen tartrate salt of the mixture; (b) fractionally crystallizing the β-isomer salt; and (c) recovering the α-isomer from the mother liquor by treatment with first a base and second a mineral acid.

9 Claims, No Drawings

RESOLUTION OF α-PIVALOYLOXYETHYL-(S)-3-(3,4-DIHYDROXY-PHENYL)-2-METHYLALANTINATE INTO ITS α AND β ISOMERS

BACKGROUND OF THE INVENTION

The preparation of a mixture of the α and β isomers of α-pivaloyloxyethyl-(S)-3-(3,4-dihydroxyphenyl)-2-methylalaninate (POE Ester) has been described by W. A. Saari, et al., *Journal of Medicinal Chemistry*, 21, 746 (1978) and U.S. Pat. No. 3,983,138 who also discloses a process for the resolution of this α/β-isomer mixture to obtain only the α-isomer in its pure state as the hydrochloride salt.

SUMMARY OF THE INVENTION

This invention relates to a novel and economical process for resolving the (α),(β)isomeric mixture of α-pivaloyloxyethyl-(S)-3-(3,4-dihydroxyphenyl)-2-methylalaninate (POE Ester) into highly pure α- and β-isomers. This invention further relates to the resolution of the POE Ester into its α- and β-isomers in the form of their highly pure, crystalline hydrogen tartrate salts enabling them to be readily compounded into suitable pharmaceutical formulations. Isolation of the α and β free base POE Ester compounds allows for great versatility in the formation of other pharmaceutically acceptable salt derivatives.

The resolution process of the instant invention generally includes fractional crystallization of the β-isomer of the POE Ester as its (+)-hydrogen tartrate salt; and, crystallization of the α-isomer from the residual mixture of α- and β-isomer (+) tartrates as its hydrochloride dihydrate salt.

Thus there is provided a process for resolving α-pivaloyloxyethyl-(S)-3-(3,4-dihydroxyphenyl)-2-methylalaninate (POE Ester) into its α- and β-isomers which comprises (a) forming a mixture of α-isomer POE Ester- and β-isomer POE Ester-d(+)-hydrogen tartrate salts; (b) isolating said β-isomer-(+)-hydrogen tartrate salt from said mixture by fractional crystallization, leaving mother liquor containing α- and β-isomer(+)-tartrate salts; and (c) treating said mother liquor from step (b) with first a base and second a mineral acid to form the crystalline α-isomer POE Ester mineral acid salt.

DETAILED DESCRIPTION OF THE INVENTION

The following flow sheet outlines the resolution process of the instant invention.

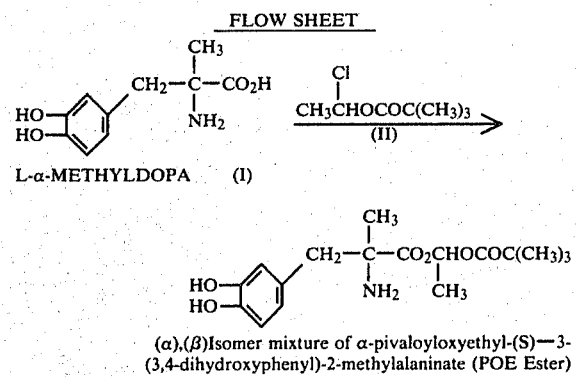

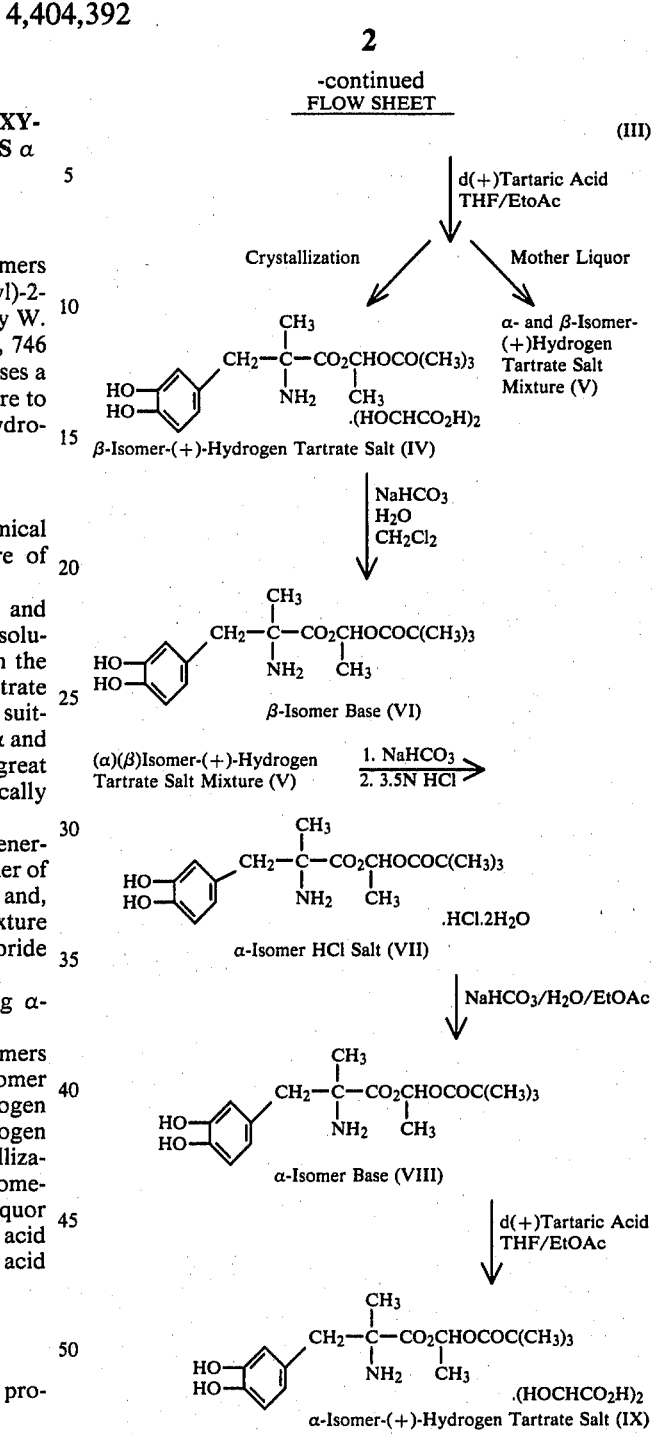

With reference to the Flow Sheet shown above, the resolution process of the invention more particularly includes preparing the α/β-isomer mixture by treating L-α-methyl-3,4-dihydroxyphenylalanine (L-α-Methyldopa) (I) with α-chlorethylpivalate (II) in a suitable solvent according to the method described by W. A. Saari, et al., supra, which is incorporated herein by reference. A suspension of the resulting α/β-isomer mixture (III) is then dissolved in an organic solvent; for example, ethyl acetate with tetrahydrofuran containing d(+)-tartaric acid and cooled to below 0° C., preferably to −12° C., to separate the isomer mixture into the crystalline and therefore mostly insoluble, β-isomer-(+)-hydrogen tartrate salt (IV) and the soluble α-isomer salt containing some of the β-isomer-(+)-hydrogen tartrate salt (V). The crystalline β-isomer-(+)-hydrogen tartrate salt (IV) may then be isolated and dissolved in water and shaken with a mixture of sodium bicarbonate and dichloromethane to provide a base solution which is then crystallized to isolate the β-isomer base (IV).

The α-isomer is recovered from the mother liquor mixture of α- and β-isomer-(+)-hydrogen tartrate salts (V) by evaporating the liquor to a residue, dissolving the residue in water and removing the α-isomer base by treatment of the solution with a mild base, for example, sodium bicarbonate, and dichloromethane. The resulting dichloromethane solution is evaporated to residue and the residue is crystallized with an aqueous mineral acid, for example, cold, 3.5 N hydrochloric acid. The resultant crystalline solid is first isolated and then dried to yield the α-isomer mineral acid (hydrochloride) dihydrate salt (VII).

The α-isomer hydrochloride dihydrate salt (VII) is converted into the α-isomer base (VIII) by treatment with an aqueous solution of base, for example, by shaking it in a water/sodium bicarbonate/ethyl acetate solution followed by separating, drying and evaporating the organic phase to obtain a solid residue. This residue is then triturated with dichloromethane and hexane is added. The resulting suspension is stirred and the solid that forms is collected, washed and dried to afford the α-isomer base (VIII).

Conversion of the α-isomer base (VIII) into its (+)-hydrogen tartrate salt (IX) may be achieved by treating the α-isomer base (VIII) in a tetrahydrofuran/ethyl acetate solution with d(+)-tartaric acid. The α-isomer-(+)-hydrogen tartrate salt (IX) crystallizes upon the addition of more ethyl acetate prior to being isolated as a white solid.

The resolution process of the invention will become more clear when considered in light of the following examples which further illustrate and set forth the best mode currently known for practicing the invention. The reference numbers shown correspond to those used in the flow sheet.

EXAMPLE 1

Preparation of α/β-Isomer mixture of POE Ester (III)

A suspension of dry (S)-3-(3,4-dihydroxyphenyl)-2-methylalaninate (I) (208 g) in toluene (320 ml), hexamethylphosphoric triamide (400 ml) and α-chloroethyl pivalate (II) (180 g) was stirred under nitrogen at 100° C. until solution occurred. The solution was stirred at 60° C. for 2 hr. and then cooled and poured into chloroform (5.4 l). The reaction product was extracted into water and this solution was made alkaline (pH 8–9) by the addition of sodium bicarbonate while the ester was extracted into dichloromethane (700 ml). The dichloromethane solution was dried and concentrated in vacuo and the α-pivaloyloxyethyl-(S)-3-(3,4-dihydroxyphenyl)-2-methylalaninate (III) was caused to precipitate from the concentrate by the addition of hexane (ca.1 l). This solid was collected, washed once with hexane (500 ml) and then dried, to give 100–130 g (31–40%) of white solid; m.p. 121°-122° C. Tlc (SiO$_2$:ethyl acetate:n-butanol:formic acid:water 60:25:10:5; iodine) showed equal concentrations of α (Rf 0.6) and β (Rf 0.68) isomers; no other materials.

Found: C, 60.0; H, 7.5; N, 4.1; C$_{17}$H$_{25}$NO$_6$ requires, C, 60.2; H, 7.4; N, 4.1; IR; (nujol) 3520, 3410, 3350, 3280, 1750, 1720, 1280, 1260, 1230, 1200, 1180, 1150, 1123, 1103, 1060, 926, 870, 815, 795 and 773 cm$^{-1}$.

The hexamethylphosphoric triamide/toluene solvent may be replaced by diethylacetamide or dimethylacetamide or tetramethylurea for the alkylation reaction.

EXAMPLE 2

Separation of the α- and β-Isomers d(+)-Tartaric acid (37.9 g, 0.25 mole) dissolved in hot (60° C.) tetrahydrofuran (200 ml) was added to a suspension of the ester isomer mixture (III) of Example 1 (85.7 g, 0.25 mole) in ethyl acetate (250 ml). The resulting solution was diluted with ethyl acetate (1.45 l) and some β-isomer-(+)-hydrogen tartrate crystals (IV) (2.7 g) obtained from a prior experiment were added. These seed crystals generally appear in the solution in 24 to 48 hours at −12° C. The slowly stirred mixture was then cooled at −12° C. for six days. The solid was then collected, washed once each with ethyl acetate (250 ml) and ether (250 ml) dried at 20° C. in vacuo to give 52.5 g (85%) of the β-isomer-(+)-hydrogen tartrate salt of α-pivaloyloxyethyl-(S)-3-(3,4-dihydroxyphenyl)-2-methylalaninate (IV). Tlc showed pure β-isomer (Rf 0.68). Assay by equivalent weight: 100.7%; m.p. 165°–166° C.; single peak by high pressure liquid chromatography.

Found: C, 51.5; H, 6.3; N, 2.8; C$_{21}$H$_{31}$NO$_{12}$ requires, C, 51.5; H, 6.4; N, 2.9%.

EXAMPLE 3

Preparation of the β-Isomer Base (VI)

The β-isomer-(+)-hydrogen tartrate salt (IV) (5 g) obtained from Example 2, was dissolved in water (50 ml) and shaken with sodium bicarbonate (5 g) and dichloromethane (200 ml) in order to neutralize the salt and extract the base. The solution of the base was washed once with water (100 ml), dried over sodium sulfate and the solution concentrated in vacuo to 10 ml. The concentrate was then diluted with hexane (40 ml) and the β-isomer base (VI) was allowed to crystallize. The β-isomer base (VI) was isolated by filtration and dried to give a white solid; m.p. 120° C.

Assay by equiv. wt.: 98.9%; Tlc. showed β-isomer with a trace of α-isomer. L.C. showed 99.9 area % single peak; [α]$_{265}^{20}$=53.7° (C=1) 0.1 N hydrochloric acid; [α]$_{405}^{20}$=44.3° (C=1) 0.1 N hydrochloric acid.

Found: C, 59.7; H, 7.3; N, 4.0; C$_{17}$H$_{25}$NO$_6$ requires, C, 60.2; H, 7.4; N, 4.1%. Proton N.M.R. in deuterated methanol: (group, multiplicity) shift; (O—CH, q.) 6.78, (ArH×3, mult.) 6.7, (CH$_2$, AB-q.) 3.02 and 2.58, (CH$_3$, d) 1.43, (CH$_3$, s) 1.35, (t-Bu, s) 1.18 d.

EXAMPLE 4

Preparation of the α-Isomer Hydrochloride (VII)

The mother liquor containing the remainder of the β-isomer-(+)-hydrogen tartrate and all the α-isomer (+) hydrogen tartrate salts from Example 2 was evaporated to residue in vacuo. The residue was then dissolved in water and the base removed by sodium bicarbonate addition followed by extraction into dichloromethane. The dichloromethane solution of the base was then evaporated to residue in vacuo and the residue crystallized from cold 3.5 N aqueous hydrochloric acid (430 ml).

The solid was isolated by filtration and dried over potassium hydroxide, in vacuo to give 46.8 g (90%) of the α-isomer hydrochloride dihydrate salt of α-pivaloyloxyethyl-(S)-3-(3,4-dihydroxyphenyl)-2-methylalaninate (VII).

EXAMPLE 5

Preparation of the α-Isomer Base (VIII)

The hydrochloride dihydrate salt (VII) (254 g) obtained from Example 4 was converted into the base by shaking it in a mixture of water (200 ml), sodium bicarbonate (63 g) and ethyl acetate (2.0.1). The organic phase was separated in a separation funnel, dried and evaporated to leave a solid residue. This residue was triturated with dichloromethane (300 ml) and then hexane (400 ml) was added. The resulting suspension was stirred 30 min. and the solid collected by filtration to give, after washing once with hexane (500 ml) and drying, 200 g of α-isomer base (VIII) (96% of white solid; m.p. 140° C.).

Assay by equiv. wt.: 100%; Tlc. single spot pure α-isomer; L.C. essentially single peak; $[\alpha]_{365}^{20} = +20.1$ (C=1); $[\alpha]_{405}^{20} = +10.1$ (C=1) 0.1 N hydrochloric acid.

Found: C, 60.2; H, 7.4; N, 4.1; $C_{17}H_{25}NO_6$ requires, C, 60.2; H, 7.4; N, 4.1%. Proton N.M.R. identical to β-isomer.

EXAMPLE 6

Preparation of the α-Isomer-(+)-Hydrogen Tartrate Salt (IX)

The α-isomer base (VIII) of Example 5 was converted into its (+)-hydrogen tartrate salt (IX) by treatment in tetrahydrofuran/ethyl acetate (100 ml each) with an equimolar quantity of (+)-tartaric acid. Addition of more ethyl acetate (900 ml) caused the α-isomer of α-pivaloyl-oxyethyl-(S)-3-(3,4-dihydroxyphenyl)-2-methylalaninate (+) hydrogen tartrate salt (IX) to crystallize. This product was then isolated by filtration as a white solid m.p. 161°–162.5° C. Tlc.: Pure α-isomer, no other spots. Assay by equivalent weight: 99.9%; 99.7% pure by high pressure liquid chromatography.

Found: C, 50.7; H, 6.2; N, 2.8; $C_{21}H_{31}NO_{12}$ requires, C, 51.5; H, 6.3; N, 2.9%.

What is claimed is:

1. A process for resolving alpha-pivaloyloxyethyl-(S)-3-(3,4-dihydroxyphenyl)-2-methylalaninate (POE Ester) into its alpha- and beta-isomers which comprises:
   (a) reacting POE Ester with d(+)-tartaric acid to form a mixture of alpha-isomer POE Ester- and beta-isomer POE Ester-(+)-hydrogen tartrate salts;
   (b) isolating said beta-isomer-(+)-hydrogen tartrate salt from said mixture by fractional crystallization, leaving mother liquor;
   (c) treating said mother liquor from step (b) with first a mild base and second a mineral acid to form the crystalline alpha-isomer POE Ester mineral acid salt.

2. The process of claim 1 which further comprises:
   (aa) converting said isolated beta-isomer (+)-hydrogen tartrate salt to the beta-isomer free base by reaction with a mild base;
   (bb) converting said alpha-isomer mineral acid salt to the alpha-isomer free base by reaction with a mild base.

3. The process of claim 2 which further comprises:
   reacting said α-isomer free base with d(+)-tartaric acid and crystallizing the resulting α-isomer-(+)-tartrate salt.

4. The process of claim 1 wherein the base in step (c) is sodium bicarbonate.

5. The process of claim 1 wherein the mineral acid in step (c) is hydrochloric acid.

6. The β-isomer salt compound, (R)-1-(2,2-dimethylpropanoyloxy)ethyl-(S)-2-amino-2-methyl-3-(3,4-dihydroxyphenyl)propionate (d) (+)-hydrogen tartrate.

7. The β-isomer free base compound, (R)-1-(2,2-dimethylpropanoyloxy)ethyl-(S)-2-amino-2-methyl-3-(3,4-dihydroxyphenyl)propionate.

8. The β-isomer free base compound, (S)-1-(2,2-dimethylpropanoyloxy)ethyl-(S)-2-amino-2-methyl-3-(3,4-dihydroxyphenyl)propionate.

9. The β-isomer salt compound, (S)-1-(2,2-dimethylpropanloyoxy)ethyl-(S)-2-amino-2-methyl-3-(3,4-dihydroxyphenyl)propionate (d) (+)-hydrogen tartrate.

* * * * *

UNITED STATES PATENT AND TRADEMARK OFFICE
CERTIFICATE OF CORRECTION

PATENT NO. : 4,404,392
DATED : September 13, 1983
INVENTOR(S) : Ramon J. Alabaster and Stanley H.B. Wright It is certified that error appears in the above—identified patent and that said Letters Patent is hereby corrected as shown below:

Claim 8, column 6, line 37, "$\beta$-isomer" should be

-- $\alpha$-isomer --

Claim 9, column 6, line 40, "$\beta$-isomer" should be

-- $\alpha$-isomer --

Signed and Sealed this

Fifteenth Day of November 1983

[SEAL]

Attest:

GERALD J. MOSSINGHOFF

*Attesting Officer*    *Commissioner of Patents and Trademarks*